US009220839B2

(12) United States Patent
Basso et al.

(10) Patent No.: US 9,220,839 B2
(45) Date of Patent: Dec. 29, 2015

(54) ASSEMBLY FOR USE IN A DRUG DELIVERY DEVICE

(75) Inventors: Nils Basso, Frankfurt am Main (DE); Thomas Nagel, Thrandt (DE); René Richter, Thrandt (DE); Robert Witt, Dresden (DE); Jens Schirmer, Dresden (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 130 days.

(21) Appl. No.: 13/319,923

(22) PCT Filed: May 20, 2010

(86) PCT No.: PCT/EP2010/056970
§ 371 (c)(1),
(2), (4) Date: Apr. 17, 2012

(87) PCT Pub. No.: WO2010/133671
PCT Pub. Date: Nov. 25, 2010

(65) Prior Publication Data
US 2012/0271242 A1    Oct. 25, 2012

(30) Foreign Application Priority Data

May 20, 2009  (EP) .................................. 09006823

(51) Int. Cl.
*B67D 7/70* (2010.01)
*A61M 5/148* (2006.01)

(52) U.S. Cl.
CPC ............. *A61M 5/148* (2013.01); *A61M 5/1483* (2013.01)

(58) Field of Classification Search
CPC ................. A61M 5/19; A61M 5/204; A61M 2005/1787; A61M 11/06; A61M 15/0086; A61F 9/0026; A61B 17/00491; A61B 2017/00495; B05B 11/3081; B05B 11/3084; B65D 83/68; B65D 83/682
USPC ................. 604/110, 181, 187, 195, 200–201, 604/203–206, 218, 220, 231–238, 244, 604/82–92, 191, 192, 197, 198, 199, 207, 604/213, 407, 411–415, 131, 134–136, 138, 604/139, 146, 228, 263, 137, 93.01, 141, 604/142–144, 147, 149, 140, 70, 81, 36, 604/185
See application file for complete search history.

(56) References Cited

U.S. PATENT DOCUMENTS 2,743,042 A *  4/1956  Burgin .......................... 222/191
3,903,888 A *  9/1975  Buelow et al. ................ 604/186
(Continued)

FOREIGN PATENT DOCUMENTS

DE   10 2007 024801     11/2008
GB       2448588        10/2008
(Continued)

OTHER PUBLICATIONS

"Depressed". The Free Online Dictionary. Accessed online Jul. 15, 2013. <http://www.thefreedictionary.com/depressed>.*
(Continued)

*Primary Examiner* — Scott Medway
(74) *Attorney, Agent, or Firm* — McDonnell Boehnen Hulbert & Berghoff LLP

(57) ABSTRACT

The present invention relates to an assembly for a drug delivery device comprising a dispensing container and a reservoir container for holding a fluid medicinal product, wherein the dispensing container and the reservoir container are connected to one another and are in fluid communication, and wherein the dispensing container is squeezable for dispensing a dose of the fluid medicinal product from the dispensing container, the dispensing container being refillable with the fluid medicinal product from the reservoir container.

9 Claims, 1 Drawing Sheet

(56) References Cited

U.S. PATENT DOCUMENTS

| | | | |
|---|---|---|---|
| 4,291,685 A * | 9/1981 | Taelman | 601/17 |
| 4,971,470 A * | 11/1990 | Moeck et al. | 401/150 |
| 5,163,909 A | 11/1992 | Stewart | |
| 5,208,933 A * | 5/1993 | Lustig et al. | 15/22.1 |
| 5,918,995 A * | 7/1999 | Puurunen | 401/146 |
| 6,126,642 A * | 10/2000 | Kriesel et al. | 604/207 |
| 6,406,207 B1 | 6/2002 | Wiegner et al. | 401/272 |
| 6,764,467 B1 * | 7/2004 | Roby et al. | 604/191 |
| 6,948,875 B1 * | 9/2005 | Jang | 401/146 |
| 8,034,044 B2 * | 10/2011 | Lee | 604/518 |
| 8,087,843 B2 * | 1/2012 | Ottaviani et al. | 401/188 R |
| 8,506,196 B2 * | 8/2013 | Boyd et al. | 401/198 |
| 2002/0177819 A1 * | 11/2002 | Barker et al. | 604/232 |
| 2007/0110503 A1 * | 5/2007 | Glover | 401/134 |

FOREIGN PATENT DOCUMENTS

| | | |
|---|---|---|
| JP | 2002-58739 A | 9/2003 |
| JP | 3721777 B2 | 11/2005 |
| WO | 01/51108 | 7/2001 |

OTHER PUBLICATIONS

European Search Report for EP Application No. 09006823, dated Dec. 30, 2009.

International Search Report for International Application No. PCT/EP2010/056970, completed Oct. 20, 2010.

English translation of Japanese Examination Report for JP App. No. 2012-511292, dated May 13, 2014.

* cited by examiner

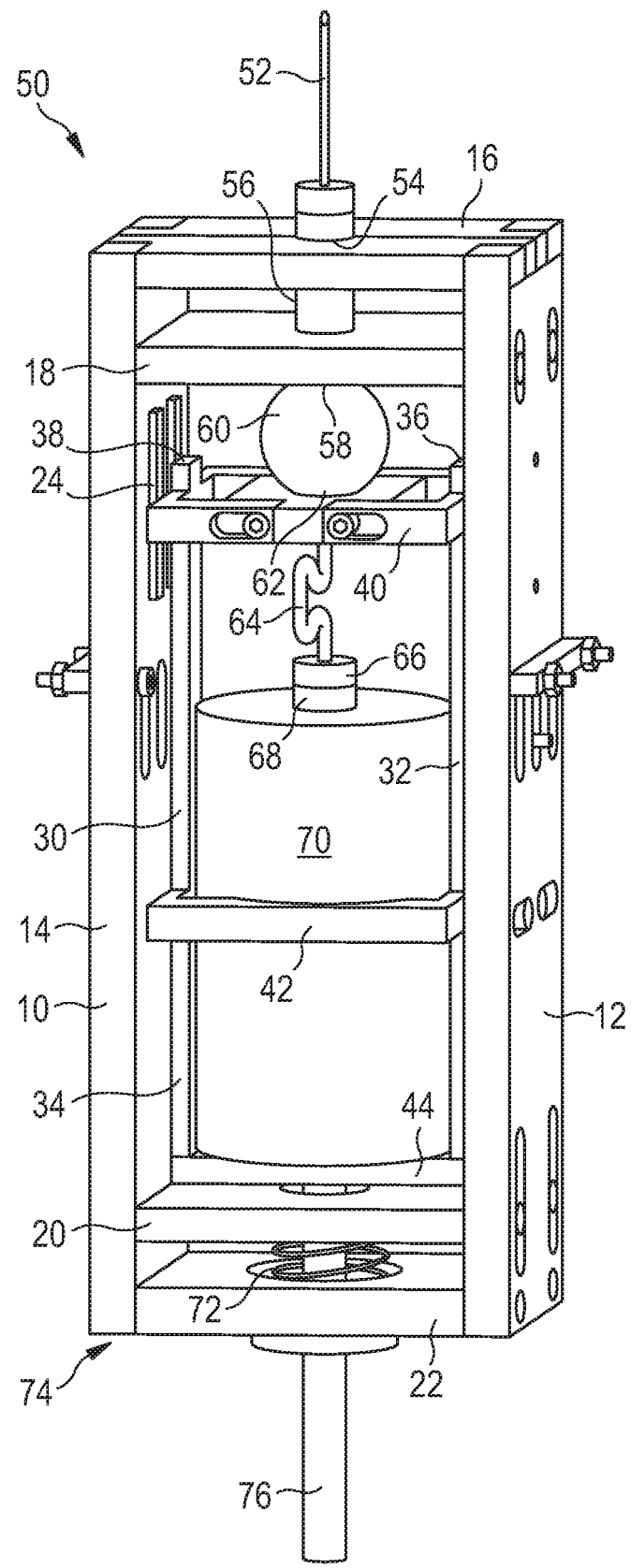

ASSEMBLY FOR USE IN A DRUG DELIVERY DEVICE

CROSS REFERENCE TO RELATED APPLICATIONS

The present application is a U.S. National Phase Application pursuant to 35 U.S.C. §371 of International Application No. PCT/EP2010/056970 filed May 20, 2010, which claims priority to European Patent Application No. 09006823.0 filed on May 20, 2009. The entire disclosure contents of these applications are herewith incorporated by reference into the present application.

FIELD OF INVENTION

The present invention relates to an assembly for use in a drug delivery device.

BACKGROUND

Drug delivery devices are generally known for the administration of a medicinal product, for example insulin, but also for other medicinal products for self-administration by a patient. Therefore, the drug delivery devices should be safe and comfortable in use and should dispense an exact dose of a medicinal product. Most of the drug delivery devices are pen-type injectors which can dispense a pre-set dose of a medicinal product.

In some cases it is necessary for the patient to get an exact volume of a certain medicinal product. In most commercially available drug delivery devices there are many sources of error for dispensing inaccuracy. One is for example the dripping out of the needle after injection and therefore the need to keep the needle in the skin after injection.

SUMMARY

It is an object to the present invention to provide an assembly for use in a drug delivery device which helps to improve the accuracy of a dispensed dose.

According to a first aspect of the present disclosure an assembly for a drug delivery device is provided, the assembly comprising a dispensing container and a reservoir container for holding a fluid medicinal product, wherein the dispensing container and the reservoir container are connected to one another and are in fluid communication, and wherein the dispensing container is squeezable for dispensing a dose of a fluid medicinal product from the dispensing container, the dispensing container being refillable with the fluid medicinal product from the reservoir container.

In the assembly, the dispensing container has an inner volume that is equivalent to a dose, whereas the reservoir container is holding a plurality of doses. The dose which may be enclosed in the dispensing container can be dispensed in a single dispensing process or in several subsequent dispensing processes.

The dispensing container can be squeezed. While the dispensing container is squeezed the fluid medicinal product is dispensed.

The fluid medicinal product that may refill the dispensing container is contained in the reservoir container. The reservoir container and the dispensing container can have a permanent connection. This connection is constructed such that the dispensing container can be refilled with fluid medicinal product from the reservoir container.

Some parts of the assembly, like for example the dispensing container, the reservoir container or the connecting means are in direct contact with the fluid medicinal product. These parts have an appropriate chemical resistance towards the fluid medicinal product that is contained. These materials can comprise PVC, silicone rubber or fluoropolymer.

In a preferred embodiment a connecting means is connecting an inlet of the dispensing container with a first outlet which is located at the reservoir container.

The connecting means can for example be a tube. A tube allows a fluid communication between the reservoir container and the dispensing container.

The connecting means can be flexible. In case that the connecting means is flexible it can provide a durable connection even if the distance between the dispensing container and the reservoir container varies during the dispensing process.

In another preferred embodiment, a first control member is located in a connecting flow path between the dispensing container and the reservoir container.

The first control member may be a check valve. This check valve can regulate the flow of the fluid medicinal product.

This regulation may affect the amount of fluid medicinal product, the time frame in which the fluid medicinal product can flow through the connecting means and the direction in which the fluid medicinal product can flow.

The control member may be located at the first outlet of the reservoir container or at the inlet of the dispensing container. Alternatively, the control member can be located somewhere between the first outlet of the reservoir container and the inlet of the dispensing container.

In one embodiment the first control member allows the fluid medicinal product to flow only from the first outlet which is located at the reservoir container in the direction of the inlet of the dispensing container.

In this embodiment a check valve may find use, wherein the medicinal product can flow through an opening in the check valve. The fluid medicinal product can only flow through the opening in a certain direction after a certain pressure is applied to the check valve.

Due to the one-way behavior of the check valve a reflow of medicinal product from the dispensing container into the reservoir container can be effectively avoided. This leads to an improved accuracy of the dosage dispensed from the dispensing container because the enclosed volume of the fluid medicinal product in the dispensing container is exactly defined.

In another embodiment a second control member is located in a dispensing flow path of a second outlet which is located at the dispensing container.

The dispensing flow path of the second outlet which is located at the dispensing container is directed towards the dispensing end of the assembly. A needle unit can be attached to this dispensing end.

The second control member may be a check valve which allows the fluid medicinal product to flow only in the dispensing direction which means from the dispensing container in the direction where the needle unit might be attached to the assembly.

In another preferred embodiment the second control member is preventing in taking of air or fluid or tissue into the dispensing container via the dispensing flow path.

In taking of air or of tissue through the second outlet would lead to a dose inaccuracy for the next dose which is dispensed from the assembly. Only the fluid medicinal product from the reservoir container should refill the dispensing container, therefore the second control member should prevent that dispensed fluid or blood flows back into the dispensing container.

One advantage of having a second control member is that the same volume of fluid medicinal product is enclosed inside the dispensing container before a dispensing process is started and after the fluid medicinal product dispensed during this dispensing process is refilled from the reservoir container.

In one preferred embodiment the second control member allows the fluid medicinal product to be dispensed through the second outlet which is located at the dispensing container.

The second outlet can be located diametrically opposed to the inlet of the dispensing container. In particular, a pen-type injector can be formed through a linear alignment of the components of the assembly.

While dispensing the fluid medicinal product the second control member opens the flow path in direction of a needle unit which might be attached. The injection takes place by means of the attached needle unit.

In another preferred embodiment the dispensing container comprises a hollow body.

The hollow body can for example be formed as a hollow sphere. The inner volume of this hollow body is equivalent to the maximum volume that can be dispensed at a time.

The dispensing container can also be pear-shaped.

In one preferred embodiment the dispensing container is elastically deformable for dispensing a dose of the fluid medicinal product.

To dispense the fluid medicinal product, a force is applied by a means that deforms the dispensing container. This force leads to an increasing deformation of the dispensing container and therefore to an increasing dispensed volume of the fluid medicinal product.

Due to the elastic condition of the dispensing container this deformation is reversible. As the force is no longer applied to the dispensing container, it returns to its original shape and size.

In another embodiment the assembly comprises a housing and an actuator which is moveable with respect to the housing.

Inside the housing, a base frame can be located which is moveable with respect to the housing. The actuator can be located at the distal end of that base frame. This actuator can be located between the reservoir container and the dispensing container. However, any other suitable position for the actuator is possible.

The housing forms a good protection for the dispensing container and for the reservoir container. The reservoir container can be attached to the base frame.

In one preferred embodiment the actuator is located at the dispensing container for dispensing the fluid medicinal product.

The actuator applies a force to the dispensing container. Due to the applied force the fluid medicinal product is dispensed. Therefore a mechanical contact is needed between the actuator and the dispensing container to apply the force to the dispensing container.

In another preferred embodiment the actuator squeezes the dispensing container and is dispensing the fluid medicinal product.

The actuator applies a force to the dispensing container as it is pushed towards the dispensing container. The container is deformed and the fluid medicinal product which is contained inside the dispensing container can be dispensed through an outlet.

The force which is applied to the dispensing container can be generated mechanically or electrically. Therefore, a dispensing means comprising a spring can be located at the distal end of the base frame. The dispensing means may be connected to the base frame. The actuator can be moved electrically or by being actuated by the user. The actuator can be moved back to the starting position by means of the spring.

The dispensing container can dispense a predefined dose of the fluid medicinal product.

In another preferred embodiment the assembly comprises a dispensing container which is expanding after dispensing the fluid medicinal product. Through the expansion a depression is created in the dispensing container which is able to intake fluid medicinal product from the reservoir container.

After the fluid medicinal product is dispensed, a depression is created inside the dispensing container. As no air can be intaken by the second outlet located at the dispensing container by means of a check valve, only fluid medicinal product from the dispensing container can flow into the dispensing container.

The depression is formed by means of the elastically deformable dispensing container. After being deformed the material tends to return to its original shape and size. The fluid from the reservoir container flows into the dispensing container because of the low pressure inside the dispensing container. During this re-shaping and refilling process the actuator and therefore the base frame may be pushed back to its starting position.

Another advantage of the depression is that the dripping time of a needle after the injection is reduced.

In another preferred embodiment the assembly comprises additional means adapted to refill the dispensing container after dispensing the fluid medicinal product.

The additional means may for example be a pump. The pump is attached to refill the dispensing container.

BRIEF DESCRIPTION OF THE FIGURES

In the following, the invention is described in further detail with reference to the drawings, wherein FIG. 1 shows a view of the assembly in a starting position.

DETAILED DESCRIPTION

In FIG. 1, identical reference numerals denote identical or comparable components.

FIG. 1 shows an assembly according to the present disclosure. The assembly is surrounded by a housing 10. The housing 10 comprises a right side member 12, a left side member 14, a distal bar 16, a first bar 18, a second bar 20 and a proximal bar 22. All of these bars 16, 18, 20, 22 comprise a central bore.

A base frame 30 is arranged inside the housing 10 which comprises a bearing in which the base frame 30 is movable in axial direction with respect to the housing 10. The base frame 30 comprises a right longitudinal bar 32, a left longitudinal bar 34, a front face 36 of the right longitudinal bar, a front face 38 of the left longitudinal bar, an actuator bar 40, a support bar 42 and a proximal bar 44 of the base frame.

The actuator bar 40 comprises a bore. A tube 64 is arranged inside this bore. A check valve is arranged inside the tube 64. The tube 64 is connecting the reservoir container 70 and the dispensing container 60.

A needle unit 52 is adapted to the distal end 50 of the assembly. The needle unit 52 is seated over a second control member 54.

The second control member 54 is located in the flow path between an intermediate member 56 and the needle unit 52. The first bar 18 of the housing 10 is located between the intermediate member 56 and the outlet 58 of the spherical body of the dispensing container 60. The center of the first bar 18 comprises a bore to allow for a flow path between the dispensing container 60 and the needle unit 52 passing through the first bar 18.

At the proximal end 74 of the dispensing container 60, an actuator bar 40 is located which comprises a small bore to define an aperture for a tube 64 which is connecting the dispensing container 60 with a reservoir container 70. On the right and on the left side of the actuator bar 40 the front faces 36, 38 of two longitudinal bars are shown. These front faces 36, 38 are not flush with the surface of the actuator.

A first control member 66 is arranged at a first outlet 68 located at the reservoir container 70. The reservoir container 70 is surrounded and connected to a support bar 42 of the base frame 30 which is comprising a central opening. This ensures a secure connection of the reservoir container 70 to the housing 10.

At the proximal bar 44 of the base frame 44, dose dispensing means 76 are shown which comprise a spring 72.

By pressing the dose dispensing means 76, the base frame 30 is pushed towards the distal end 50 of the housing 10. This movement causes a compression of the dispensing container 60 and liquid medicinal product is dispensed through the needle unit 52.

The distal movement is stopped by the abutment of the front faces 36, 38 of the longitudinal bars of the base frame 30 with the first bar 18 of the housing 10. The abutment indicates that the maximum dosage of the medicinal product is dispensed. This is the final position of the base frame during the dispensing process.

Due to the elastic behavior of the dispensing container 60, the dispensing container 60 is withdrawing fluid medicinal product from the reservoir container 70 by suction. This process ends after the dispensing container 60 has reached its original shape.

The check valve 54 ensures that just the fluid medicinal product from the reservoir container 70 is flowing into the dispensing container 60 by closing the dispensing flow path in proximal direction 74. This is an effective method to prevent the intaking of air, tissue or blood into the dispensing container 60.

The spring 72 at the proximal end 74 of the assembly together with the elastic behavior of the dispensing container 60 after dispensing the fluid medicinal product enables the base frame 30 to be pushed back in proximal direction 74. After the dispensing container 60 is refilled, the movement of the base frame 30 ends in its starting position.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An assembly for a drug delivery device comprising
a housing having a right side member and a left side member;
a dispensing container mounted within the housing and configured for holding a single dose of a fluid drug product;
a reservoir container having a first outlet, mounted within the housing and holding a plurality of doses of the fluid drug product, wherein the dispensing container and the reservoir container are connected to one another, are in fluid communication and are both completely contained between the right side member and the left side member of the housing; and
an actuator movably positioned between the dispensing container and the reservoir container and completely contained within the housing and configured to apply a squeezing force to the dispensing container for dispensing the single dose of the fluid drug product from the dispensing container through a second outlet, where the actuator moves relative to the housing during dispensing,
wherein the dispensing container is refillable with doses of the fluid drug product from the reservoir container through a first one way check valve in fluid communication with the dispensing container that prevents fluid movement from the dispensing container into the reservoir container.

2. An assembly for a drug delivery device according to claim 1, wherein a tube connects an inlet of the dispensing container with the first outlet which is located at the reservoir container.

3. An assembly for a drug delivery device according to claim 1, wherein a second one way check valve is located in a dispensing flow path of the second outlet which is located at the dispensing container.

4. An assembly for a drug delivery device according to claim 3, wherein the second one way check valve prevents intaking of air or fluid or tissue into the dispensing container via the dispensing flow path.

5. An assembly for a drug delivery device according to claim 3 wherein the second one way check valve allows the fluid drug product to be dispensed through the second outlet which is located at the dispensing container.

6. An assembly for a drug delivery device according to claim 1, wherein the dispensing container comprises a hollow body.

7. An assembly for a drug delivery device according to claim 1, wherein the dispensing container is elastically deformable for dispensing a dose of the fluid drug product.

8. An assembly for a drug delivery device according to claim 1, wherein the actuator is located at the dispensing container for dispensing the fluid drug product.

9. An assembly for a drug delivery device according to claim 1, wherein the dispensing container is expanding after dispensing the fluid drug product and is, by means of a depression created in the dispensing container able to intake fluid drug product from the reservoir container.

* * * * *